US010697890B1

(12) United States Patent
Bailey et al.

(10) Patent No.: US 10,697,890 B1
(45) Date of Patent: Jun. 30, 2020

(54) APPARATUS AND METHOD OF HYDROXYL DETECTION

(71) Applicant: United States of America as represented by the Administrator of NASA, Washington, DC (US)

(72) Inventors: Steven A. Bailey, Gambrills, MD (US); Thomas F. Hanisco, Takoma Park, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 117 days.

(21) Appl. No.: 16/143,762

(22) Filed: Sep. 27, 2018

(51) Int. Cl.
*G01N 21/33* (2006.01)
*G01N 21/25* (2006.01)
*G01N 33/00* (2006.01)

(52) U.S. Cl.
CPC ........... *G01N 21/33* (2013.01); *G01N 21/255* (2013.01); *G01N 33/0036* (2013.01); *G01N 2201/0233* (2013.01); *G01N 2201/0636* (2013.01); *G01N 2201/0648* (2013.01)

(58) Field of Classification Search
CPC ... G01N 21/33; G01N 21/255; G01N 33/0036
USPC .......................................................... 250/373
See application file for complete search history.

(56) References Cited

U.S. PATENT DOCUMENTS 7,425,452 B2 * 9/2008 Kajii .................. G01N 21/6404
250/373

* cited by examiner

*Primary Examiner* — Edwin C Gunberg
(74) *Attorney, Agent, or Firm* — Heather Goo; Bryan A. Geurts

(57) ABSTRACT

The present invention relates to measuring hydroxyl in an atmosphere, including forwarding sunlight and ultraviolet light into a gas cell; switching between nitrogen gas only, or nitrogen gas and water vapor, into the gas cell; emitting ultraviolet rays into the cell which breaks down the water vapor into hydroxyl; and detecting a difference between two states, including 1) an OFF state where only nitrogen gas does not react to the ultraviolet light or the sunlight and there is no OH filter and the detector detects light that OH absorbs; and 2) an ON state where the water vapor is broken down by the ultraviolet rays to produce hydroxyl, and the gas cell acts as an OH filter and does not detect the light that OH absorbs; where a difference in signals measured by the detector in the two states is proportional to a column abundance of OH in earth atmosphere.

16 Claims, 4 Drawing Sheets

APPARATUS AND METHOD OF HYDROXYL DETECTION

ORIGIN OF THE INVENTION

The invention described herein was at least in-part made by an employee of the United States Government and may be manufactured or used by or for the Government of the United States of America for governmental purposes without the payment of any royalties thereon or therefor.

BACKGROUND OF THE INVENTION

1. Field of the Invention

The present invention relates to a novel apparatus and method of measuring hydroxyl (OH) which includes combining some properties of water ($H_2O$) Gas Correlation Radiometry (GCR) as a precise bandpass filter to detect OH absorption in the atmosphere.

2. Description of the Related Art

Hydroxyl is an important greenhouse gas that is difficult to measure as it reacts with everything (including itself). The hydroxyl radical (OH) determines the atmospheric lifetime of methane. Despite the increasing importance of methane, there is no airborne or space-based measurement of the OH column abundance.

Given its short lifespan (due to this reactivity), to measure it, one must generate it (actively) to use as a reference. Current estimates of OH columns are based on models. Also, given its reactivity, one is limited by the amount that can be generated. Since these small amounts are not useful, increasing the path length of the measurement is the mitigation.

Accordingly, it is important to provide remote measurements of the atmospheric OH column (between earth surface and top of the atmosphere), and a method of measuring hydroxyl, which is easier and simpler than current methods is desired.

SUMMARY OF THE INVENTION

The present invention relates to a novel apparatus and method of measuring hydroxyl (OH), which includes combining some properties of water ($H_2O$) Gas Correlation Radiometry (GCR) as a precise bandpass filter to detect OH absorption in the atmosphere.

In one embodiment, the present invention describes an apparatus, which measures hydroxyl in an atmosphere, that includes a gas cell having a cavity; a sunlight forwarding mechanism, which forwards sunlight into the gas cell; an ultraviolet light forwarding mechanism, which forwards ultraviolet light into the gas cell; a nitrogen gas source, which produces nitrogen gas and a water vapor source which produces water vapor; a switch that switches between the nitrogen gas only, or the nitrogen gas and the water vapor in combination, each of which are flowed alternatingly into the gas cell; an ultraviolet lamp, which emits ultraviolet rays into the cavity and which breaks down the water vapor into hydroxyl; and a detector that detects a difference between two states, including: an OFF state where the water vapor source is switched off and where only nitrogen gas is flowed into the gas cell, the nitrogen gas which does not react to the ultraviolet light or the sunlight and there is no OH filter and the detector detects light that OH absorbs; and an ON state where the water vapor is switched on and the water vapor is broken down by the ultraviolet rays of the ultraviolet lamp to produce hydroxyl, and the gas cell acts as an OH filter and does not detect the light that OH absorbs; wherein a difference in signals measured by the detector in the two states is proportional to a column abundance of OH in earth atmosphere.

In one embodiment, the sunlight forwarding mechanism, which forwards the sunlight, includes a suntracker, which tracks the sun and forwards the sunlight to an optical chopper, which modulates the sunlight to remove any background signal; a shutter for the sunlight; and a reflector, which reflects half of the sunlight to the gas cell.

In one embodiment, the ultraviolet light forwarding mechanism, which forwards the ultraviolet light, includes an ultraviolet light emitting diode (LED), which produces the ultraviolet light; and a shutter for the ultraviolet light. The reflector reflects half of the ultraviolet light to the gas cell.

In one embodiment, the sunlight provides for OH column measurement and the ultraviolet LED provides for calibration.

In one embodiment, the ultraviolet LED is a 308 nm light-emitting diode.

In one embodiment, the gas cell provides an effective optical path of 500 m in a 0.5 m footprint; and the optical path of 500 m is optically thick at OH wavelengths.

In one embodiment, the gas cell includes a plurality of reflective mirrors.

In one embodiment, the apparatus further includes a vacuum pump which removes the nitrogen gas and the water vapor from the gas cell.

In one embodiment, a method of measuring hydroxyl in an atmosphere includes forwarding sunlight from the sun into a gas cell having a cavity; forwarding ultraviolet light from the LED into the cavity of the gas cell; forwarding nitrogen gas from a nitrogen gas source, and water vapor from a water vapor source, into the cavity of the gas cell; switching between the nitrogen gas only, or the nitrogen gas and the water vapor in combination, into the gas cell; breaking down the water vapor into hydroxyl using an ultraviolet lamp which emits ultraviolet rays into the cavity; and detecting a difference between two states, to measure the hydroxyl. The two states include detecting light that OH absorbs in an OFF state where there is no OH filter, and in an ON state where there is an OH filter. In the OFF state, the water vapor source is switched off and only nitrogen gas is flowed into the gas cell, the nitrogen gas which does not react to the ultraviolet light or the sunlight; and wherein in the ON state, the water vapor is switched on and the water vapor is broken down by the ultraviolet rays to produce the hydroxyl, and the gas cell does not detect the light that OH absorbs; and wherein a difference in signals measured by the detector in the two states is proportional to a column abundance of OH in earth atmosphere.

In one embodiment, the method further includes chopping the sunlight using an optical chopper to modulate the sunlight and remove any background signal; and reflecting a half of the sunlight to the gas cell.

In one embodiment, the method further includes producing the ultraviolet light using an ultraviolet LED; and reflecting a half of the ultraviolet light to the gas cell.

In one embodiment, the sunlight provides for OH column measurement and the ultraviolet LED provides for calibration.

In one embodiment, the ultraviolet LED is a 308 nm light-emitting diode.

In one embodiment, the gas cell provides an effective optical path of 500 m in a 0.5 m footprint. The optical path of 500 m is optically thick at OH wavelengths.

In one embodiment, the method further includes removing the nitrogen gas and the water vapor from the gas cell using a vacuum pump.

Thus, as has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The descriptions of the drawings are only one exemplary embodiment of the disclosure and not to be considered as limiting in scope.

DESCRIPTION OF THE INVENTION

The present invention relates to a novel apparatus and method of measuring hydroxyl (OH) which includes combining some properties of water ($H_2O$) Gas Correlation Radiometry (GCR) as a precise bandpass filter to detect OH absorption in the atmosphere.

Figure 1:
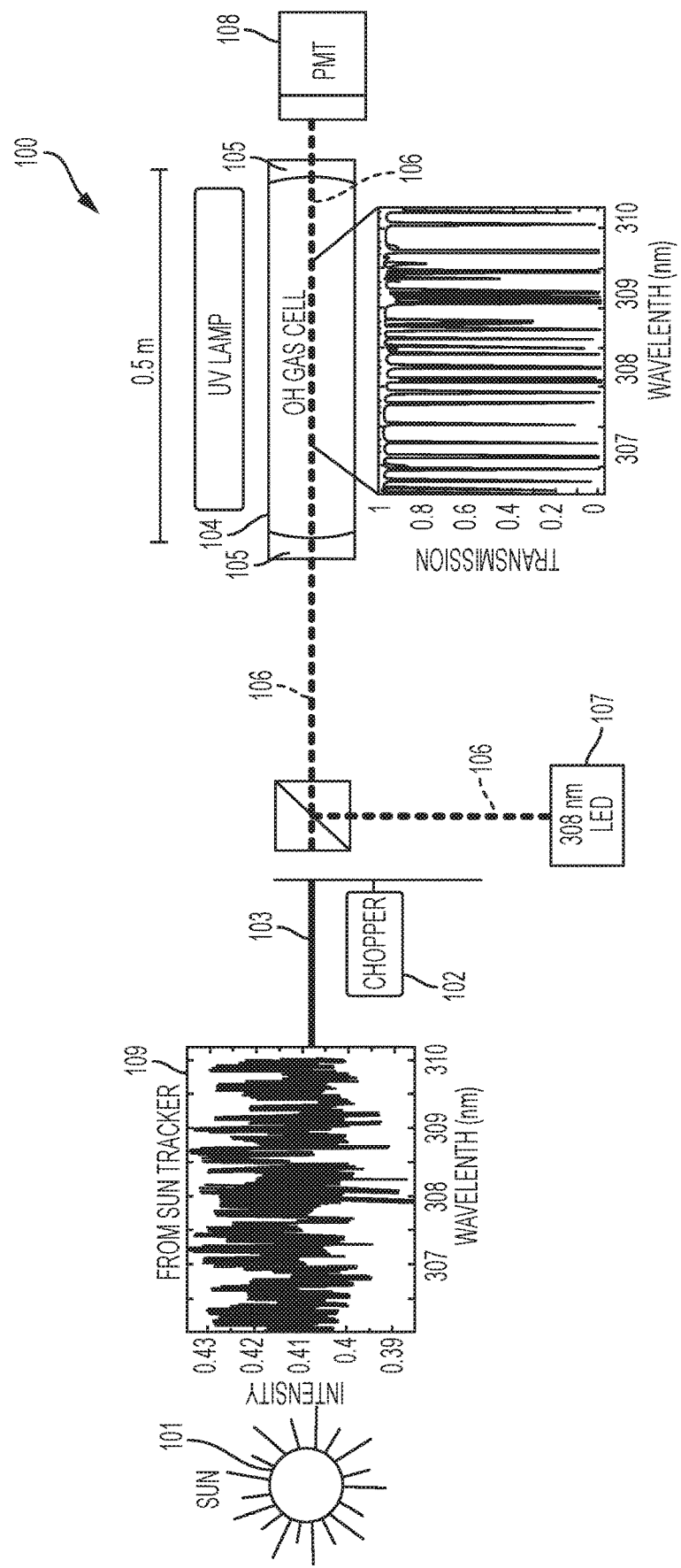
FIG. 1 is a schematic diagram of the apparatus to measure hydroxyl (OH) with emphasis on the specific wavelengths at which atmospheric OH is detected, according to one embodiment consistent with the present invention.

In one embodiment, the present invention is directed to a cavity-enhanced gas filter radiometer 100 (see FIG. 1) that selectively detects atmospheric hydroxyl (OH). Hydroxyl (OH) is a trace gas that absorbs strongly at specific wavelengths in the ultraviolet.

In one embodiment, to measure this absorption remotely, the present invention utilizes the sun as a light source 101. By pointing an optical collector (telescope) at the sun 101, the sunlight is forwarded via a sun tracker 109, such as an EKO Model STR-21G Sun Tracker or the like, through an optical chopper 102 to modulate the light 103. In one embodiment, this modulated light is then forwarded to a cavity enhanced gas cell 104 made from highly reflective mirrors 105, which forms part of the central technology of the present invention.

In one embodiment, hydroxyl (OH) is generated from water ($H_2O$) and exposure to ultraviolet (UV) light from the UV lamp 313. The 500 m path gas cell 104 is optically thick (i.e., optical depth) at OH wavelengths.

More specifically, in one embodiment, the gas cell 104 provides an effective optical path of 500 m in a 0.5 m footprint. This cavity enhanced cell 104 provides a mechanism of blocking light at wavelengths that OH absorbs. It acts as a high fidelity optical filter 100 that can be switched "ON" and "OFF" to provide a difference signal for a measurement of atmospheric OH.

Figure 3:
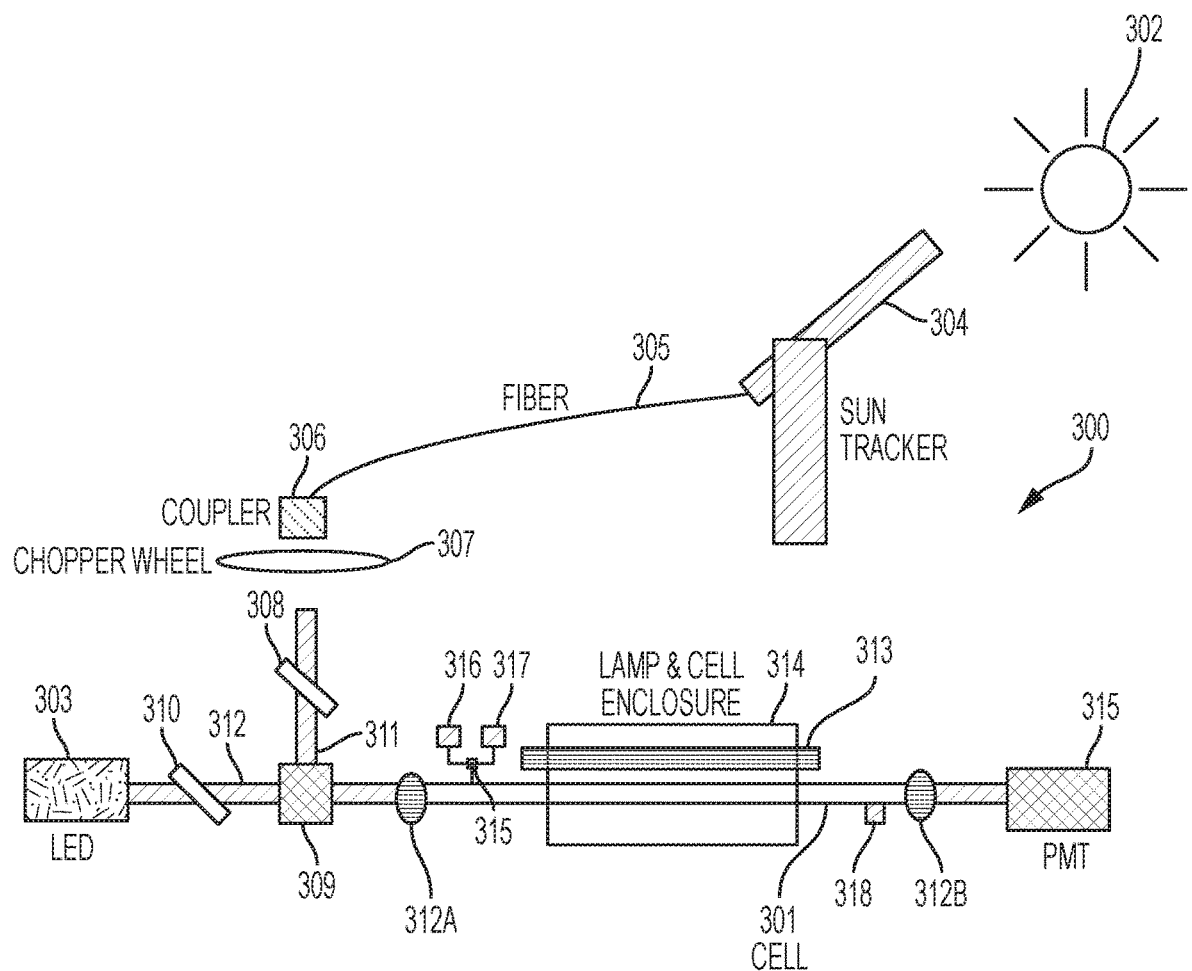
FIG. 3 is a schematic diagram of the major components of the apparatus for detecting hydroxyl (OH) according to one embodiment consistent with the present invention.

In one embodiment, as shown in FIG. 3, the two states ("ON"/"OFF") of the OH radiometer 100, include alternating (using a switch 315) the contents of the gas cell 104 between nitrogen gas only from nitrogen gas cell 316, or nitrogen gas from cell 316 and water vapor from water vapor cell 317. In one embodiment, the two states (in two iterations) are measured in a 40 second measurement cycle, with each iteration occurring in 10 second intervals.

Figure 2A:
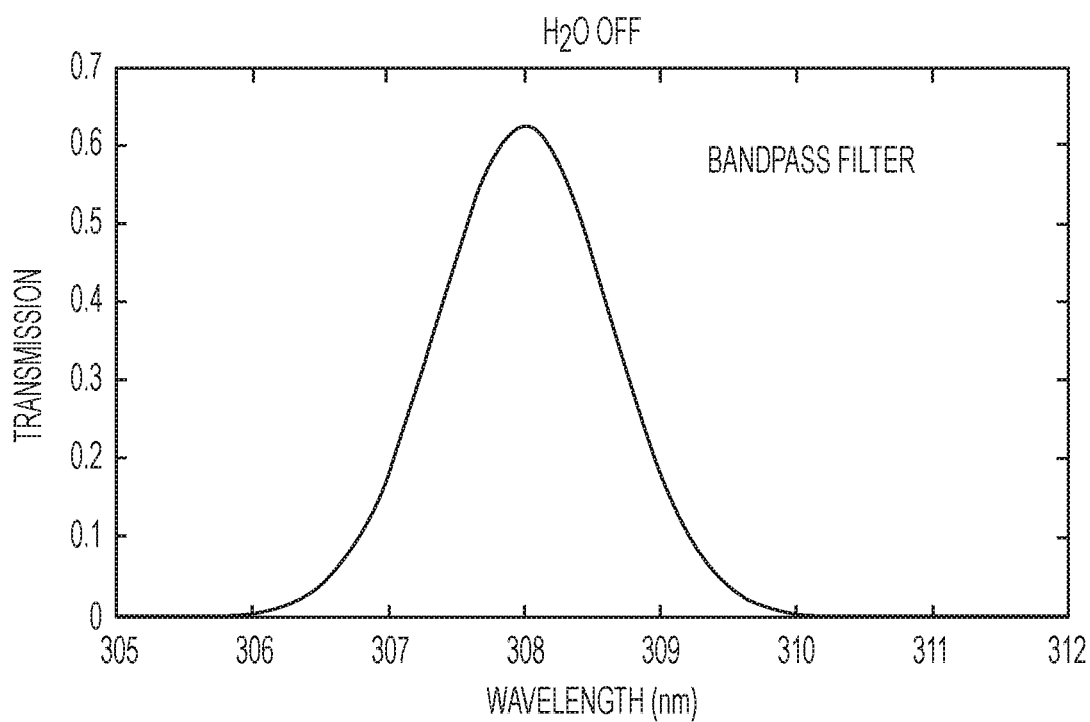
FIG. 2A shows a wavelength graph of the hydroxyl (OH) radiometer in a first state where the water source is "OFF" and there is no OH in the gas cell and the detector is sensitive to atmospheric OH, according to one embodiment consistent with the present invention.

1) In the "OFF" state, light emitting diode (LED) shutter 310 is open, and sun shutter 308 is closed, and the water ($H_2O$) source 317 switched "OFF", and only nitrogen gas flows into the gas cell 104, 301. The nitrogen gas does not react to the ultraviolet (UV) light from the light emitting diode (LED) 107 (see FIG. 2A), so it is used as a carrier. Without water vapor (i.e., nitrogen only), there is no OH filter (see FIG. 2A). The photomultiplier tube (PMT) or detector 108, 315 sees the light that OH absorbs. Thus, the detector 108 is sensitive to atmospheric OH.

Figure 2B:
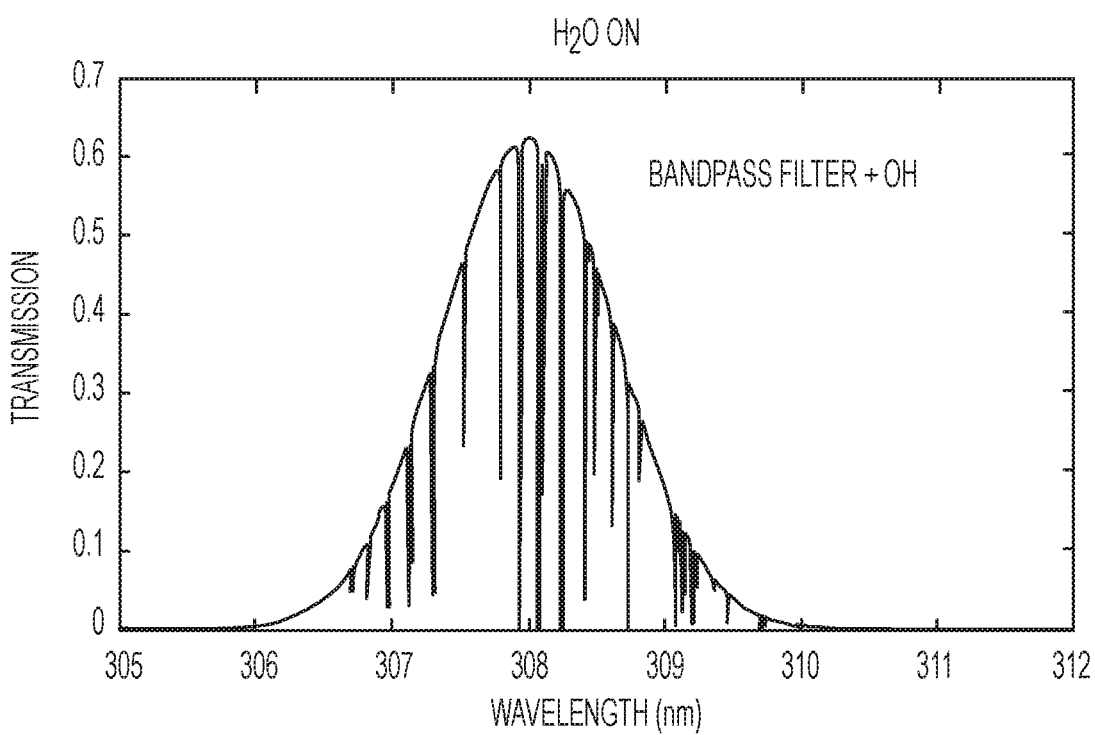
FIG. 2B shows a wavelength graph of the hydroxyl (OH) radiometer in a second state where the water source is "ON" and there is OH in the gas cell and the detector is not sensitive to atmospheric OH, according to one embodiment consistent with the present invention.

2) In the "ON" state, the LED shutter 310 is open, the sun shutter 308 is closed, and the water ($H_2O$) source 317 switched to "ON", so that water vapor is added to the nitrogen gas which flows into the cell 104, 301. The water vapor is broken down into hydroxyl (OH) by the 170 nm UV lamp 313, so the gas cell 104, 301 acts as an OH filter when water vapor is in the cell 104, 301 (see FIG. 2B). The photomultiplier tube (PMT) or detector 108, 315 does not see the light that OH absorbs. Thus, the detector 108, 315 is not sensitive to atmospheric OH.

In the next iteration of the "OFF" state, the LED shutter is closed 310 and the sun shutter is open 308 when nitrogen only flows into the gas cell 104, 301, and the nitrogen gas does not react to the sunlight 311 flowing into the cell 104, 301 and the detector 108, 315 sees the light OH absorbs.

In the next iteration of the "ON" state, the LED shutter 310 is closed and the sun shutter 308 is open when nitrogen and water vapor are flowed into the cell 104, 301, and the detector 108, 315 does not see the light the OH absorbs. The cycle then repeats.

In one embodiment, the sunlight 311 provides for OH column measurement and the LED light 312 provides for calibration.

The present invention utilizes this unique apparatus of a high-fidelity gas filter cell 104, 301 for OH, which has not been previously accomplished because OH is a highly reactive gas. It cannot be stored in a cylinder. Although OH can be made dynamically with UV light, it is extremely hard to get enough OH to absorb light in a short optical path.

Accordingly, the present invention has created a high-fidelity cell 104, 301 that filters out nearly 100% of the light at only the wavelengths that OH absorbs. A high optical depth (near 100% absorption of the light) has been obtained by the present invention at the OH wavelengths by combining an efficient OH source (UV light 107, 303+$H_2O$ source 317) with an optical pathlength of about 500 m.

The present invention utilizes some principles of broad band cavity enhanced spectroscopy (BBCEAS) to obtain the long optical path, although the present invention has improved on this prior art technique to accomplish the present invention. In fact, the present invention is the only and unique technique which has conceptualized and accomplished making a gas filter cell for sun radiometry.

Figure 4:
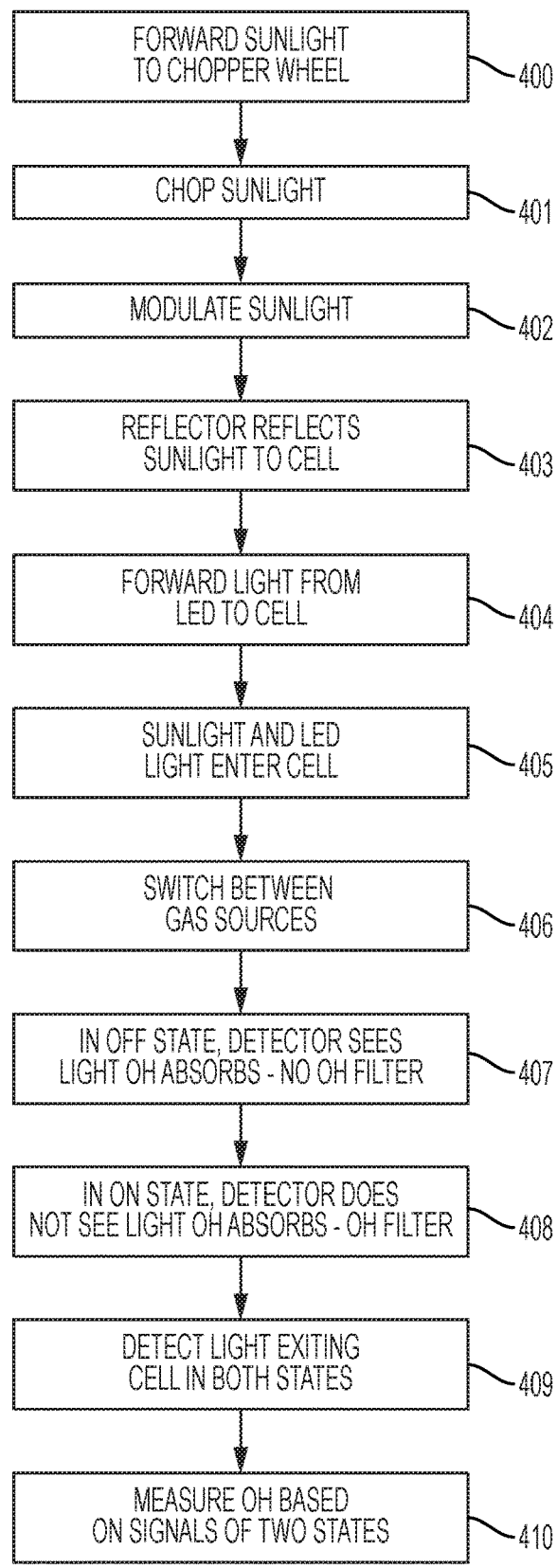
FIG. 4 is a flow chart of the method to measure hydroxyl (OH), according to one embodiment consistent with the present invention.

In one embodiment, FIG. 3 shows a more detailed setup of the OH radiometer 300 of the present invention, which uses a high-fidelity OH gas filter cell 301 to provide a measure of OH in the atmosphere by measuring the amount of sunlight absorbed by OH. The steps taken in accomplishing the present invention are also described in FIG. 4.

In step 400, a sun tracker 304 follows the sun 302 and forwards the sunlight via optical fiber 305, through coupler 306, where it is chopped by chopper wheel 307 in step 401. This modulates the light to remove any background signal, as it passed through shutter 308 to partial light reflector 309 in step 402.

In step 403, in one embodiment, light from the sun 302 hits the reflector 309 and half goes to the cell 301.

In one embodiment, in step 404, the light from the LED 303 also passes through a shutter 310, before arriving at the reflector 309 where half the light from the LED 303 goes straight to the cell 301. The LED light 312 is modulated with electrical signals when it passes through shutter 310.

In one embodiment, in step 405, the sun light 311 and LED light 312 enter the gas cell 301 cavity disposed in enclosure 314, through first mirror 312A.

In one embodiment, the OH in the cell 301 is modulated in step 406, by switching between two gas sources 316, 317—i.e., nitrogen only, or nitrogen plus water vapor, respectively. By switching the gas into the cell 301 from nitrogen (only) to nitrogen plus water vapor, two distinct states are achieved in the cavity 301.

In one embodiment, these two states are: 1) the absence of OH (with nitrogen only gas); and 2) the presence of OH (with nitrogen plus water vapor), with the LED shutter 310 first open and sun shutter 308 closed for the first two iterations and reversed for the second two iterations as described above.

In one embodiment, as noted above, in the "OFF" state, with the water ($H_2O$) source 317 switched "OFF" and only nitrogen gas in the gas cell 104, 301, the nitrogen gas does not react to the ultraviolet (UV) light from the light emitting diode (LED) 107 or the sunlight 311 in step 407, and there is no OH filter.

In one embodiment, as noted above, in the "ON" state, with the water ($H_2O$) source 317 switched on, the water vapor is added to the nitrogen gas and is broken down into hydroxyl (OH) by UV lamp 313 (i.e., $H_2O$+UV photon→OH), so the gas cell 104, 301 acts as an OH filter in step 408.

In one embodiment, the light bounces back and forth in cavity 314 (roughly 1000 times), before it leaves the cell 301. In one embodiment, light exiting the cell 301, through second mirror 312B, is detected by the detector PMT 315, in step 409. A vacuum pump 318 removes the nitrogen and water vapor from the cell 301.

In one embodiment, this detection of light in the cell 301 means that in the OFF state, the photomultiplier tube (PMT) or detector 315 sees the light that OH absorbs. Thus, the detector 315 is sensitive to atmospheric OH.

In one embodiment, in the ON state, the photomultiplier tube (PMT) or detector 315 does not see the light that OH absorbs. Thus, the detector 315 is not sensitive to atmospheric OH.

In one embodiment, the difference in the signal measured by the detector 315 in these two states (two iterations each) is proportional to the column abundance of OH in the earth's atmosphere, as measured in step 410.

With the novel technology of the present invention, one can build an OH measuring instrument that is much smaller, cheaper, and less complex than the current state of the art. The relatively low cost means that it can be duplicated to produce multiple copies. It is also small enough to be portable and simple enough to be replicated by other people/scientist/engineers.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. An apparatus which measures hydroxyl in an atmosphere, the apparatus comprising:
    a gas cell having a cavity;
    a sunlight forwarding mechanism, which forwards sunlight into said gas cell;
    an ultraviolet light forwarding mechanism, which forwards ultraviolet light into said gas cell;
    a nitrogen gas source, which produces nitrogen gas;
    a water vapor source, which produces water vapor;
    a switch which switches between said nitrogen gas only, or said nitrogen gas and said water vapor in combination, each of which are flowed alternatingly into said gas cell;
    an ultraviolet lamp, which emits ultraviolet rays into said cavity and which breaks down said water vapor into hydroxyl; and
    a detector, which detects a difference between two states, the two states including:
        an OFF state where said water vapor source is switched off and where only nitrogen gas is flowed into said gas cell, said nitrogen gas which does not react to said ultraviolet light or said sunlight and there is no OH filter and said detector detects light that OH absorbs, and
        an ON state where said water vapor is switched on and said water vapor is broken down by said ultraviolet rays of said ultraviolet lamp to produce hydroxyl, and said gas cell acts as an OH filter and does not detect said light that OH absorbs, wherein a difference in signals measured by said detector in said two states is proportional to a column abundance of OH in earth atmosphere.

2. The apparatus of claim 1, wherein said sunlight forwarding mechanism comprises
   a suntracker which tracks the sun and forwards said sunlight to an optical chopper which modulates said sunlight to remove any background signal;
   a shutter for said sunlight; and
   a reflector which reflects a half of said sunlight to said gas cell.

3. The apparatus of claim 2, wherein said ultraviolet light forwarding mechanism comprises
   an ultraviolet light emitting diode (LED) which produces said ultraviolet light; and
   a shutter for said ultraviolet light;
   wherein said reflector reflects half of said ultraviolet light to said gas cell.

4. The apparatus of claim 1, wherein said sunlight provides for OH column measurement and said ultraviolet light provides for calibration.

5. The apparatus of claim 3, wherein said ultraviolet LED is a 308 nm light-emitting diode.

6. The apparatus of claim 5, wherein said gas cell provides an effective optical path of 500 m in a 0.5 m footprint; and
   wherein said optical path of 500 m is optically thick at OH wavelengths.

7. The apparatus of claim 6, wherein said gas cell is comprised of a plurality of reflective mirrors.

8. The apparatus of claim 7, the apparatus further comprising:
   a vacuum pump which removes said nitrogen gas and said water vapor from said gas cell.

9. A method of measuring hydroxyl in an atmosphere, the method comprising:
   forwarding sunlight from the sun into a gas cell having a cavity;
   forwarding ultraviolet light into said cavity of said gas cell;
   forwarding nitrogen gas from a nitrogen gas source and water vapor from a water vapor source into said cavity of said gas cell;
   switching between said nitrogen gas only, or said nitrogen gas and said water vapor in combination, into said gas cell;
   breaking down said water vapor into hydroxyl using an ultraviolet lamp which emits ultraviolet rays into said cavity; and
   detecting a difference between two states to measure said hydroxyl, said two states including detecting light that OH absorbs in an OFF state where there is no OH filter, and in an ON state where there is an OH filter;
   wherein, in said OFF state, said water vapor source is switched off and only nitrogen gas is flowed into said gas cell, said nitrogen gas which does not react to said ultraviolet light or said sunlight; and
   wherein, in said ON state, said water vapor is switched on and said water vapor is broken down by said ultraviolet rays to produce said hydroxyl, and said gas cell does not detect said light that OH absorbs; and
   wherein a difference in signals measured by said detector in said two states is proportional to a column abundance of OH in earth atmosphere.

10. The method of claim 9, the method further comprising:
    chopping said sunlight using an optical chopper to modulate said sunlight and remove any background signal; and
    reflecting a half of said sunlight to said gas cell.

11. The method of claim 10, the method further comprising:
    producing said ultraviolet light using an ultraviolet LED; and
    reflecting a half of said ultraviolet light to said gas cell.

12. The method of claim 11, wherein said sunlight provides for OH column measurement and said ultraviolet light provides for calibration.

13. The method of claim 12, wherein said ultraviolet LED is a 308 nm light-emitting diode.

14. The method of claim 13, wherein said gas cell provides an effective optical path of 500 m in a 0.5 m footprint; and
    wherein said optical path of 500 m is optically thick at OH wavelengths.

15. The method of claim 14, the method further comprising:
    removing said nitrogen gas and said water vapor from said gas cell using a vacuum pump.

16. The method of claim 9, wherein said gas cell is comprised of a plurality of reflective mirrors.

* * * * *